(12) United States Patent
Pauker

(10) Patent No.: US 10,639,005 B2
(45) Date of Patent: May 5, 2020

(54) ENDOSCOPIC DEVICE

(71) Applicant: DIGITAL ENDOSCOPY GMBH, Friedberg (DE)

(72) Inventor: Fritz Pauker, Diedorf (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 538 days.

(21) Appl. No.: 15/329,403

(22) PCT Filed: Jul. 27, 2015

(86) PCT No.: PCT/EP2015/067155
§ 371 (c)(1),
(2) Date: Jan. 26, 2017

(87) PCT Pub. No.: WO2016/016188
PCT Pub. Date: Feb. 4, 2016

(65) Prior Publication Data
US 2017/0215839 A1 Aug. 3, 2017

(30) Foreign Application Priority Data
Jul. 28, 2014 (DE) .......................... 10 2014 214 754

(51) Int. Cl.
| | |
|---|---|
| *A61B 8/12* | (2006.01) |
| *A61B 1/00* | (2006.01) |
| *A61B 1/05* | (2006.01) |
| *A61B 8/08* | (2006.01) |
| *A61B 5/00* | (2006.01) |
| *A61M 25/10* | (2013.01) |
| *A61B 1/005* | (2006.01) |
| *A61B 8/00* | (2006.01) |

(52) U.S. Cl.
CPC ................ *A61B 8/12* (2013.01); *A61B 1/005* (2013.01); *A61B 1/00078* (2013.01); *A61B 1/00082* (2013.01); *A61B 1/05* (2013.01); *A61B 5/0051* (2013.01); *A61B 8/445* (2013.01); *A61B 8/485* (2013.01); *A61M 25/10182* (2013.11)

(58) Field of Classification Search
CPC ........................... A61B 8/12; A61M 25/10182
USPC ........................................................ 600/438
See application file for complete search history.

(56) References Cited

U.S. PATENT DOCUMENTS

| | | |
|---|---|---|
| 5,265,612 A | 11/1993 | Sarvazyan et al. |
| 5,762,066 A | 6/1998 | Law et al. |
| 6,511,427 B1 | 1/2003 | Sliwa et al. |
| (Continued) | | |

FOREIGN PATENT DOCUMENTS

| | | |
|---|---|---|
| CN | 1964670 A | 5/2007 |
| CN | 101268953 A | 9/2008 |
| (Continued) | | |

OTHER PUBLICATIONS

Office Action issued in Chinese family member Patent Appl. No. 201580041498.9, dated Nov. 3, 2017.
(Continued)

*Primary Examiner* — Nadia A Mahmood
(74) *Attorney, Agent, or Firm* — Greenblum & Bernstein, P.L.C.

(57) ABSTRACT

The invention relates to an endoscopic device to be inserted into a body cavity. The endoscopic device includes an elastographic recording means, an inflatable body, and a device for rhythmically changing the volume of the inflatable body.

12 Claims, 1 Drawing Sheet

(56) References Cited

U.S. PATENT DOCUMENTS

| | | |
|---|---|---|
| 8,696,583 B2 | 4/2014 | Ohgishi et al. |
| 9,226,647 B2 | 1/2016 | Sugawara |
| 9,332,964 B2 | 5/2016 | Miyake |
| 2002/0068870 A1 | 6/2002 | Alam et al. |
| 2004/0210136 A1 | 10/2004 | Varghese et al. |
| 2008/0033295 A1 | 2/2008 | Matsumura |
| 2009/0048489 A1 | 2/2009 | Igarashi et al. |
| 2012/0095292 A1 | 4/2012 | Gunday et al. |
| 2014/0100457 A1 | 4/2014 | Nishina et al. |

FOREIGN PATENT DOCUMENTS

| | | | |
|---|---|---|---|
| CN | 103153153 A | | 6/2013 |
| CN | 103269645 A | | 8/2013 |
| EP | 1 803 404 A1 | | 7/2007 |
| EP | 2832298 A1 | | 2/2015 |
| JP | 2001-224594 A | | 8/2001 |
| JP | 2010-82337 A | | 4/2010 |
| WO | WO2013168498 A1 | | 11/2013 |
| WO | 2013/179203 A1 | | 12/2013 |
| WO | 2014/112168 A1 | | 7/2014 |

OTHER PUBLICATIONS

Office Action issued in German family member Patent Appl. No. 10 2014 214 754.9, dated Feb. 22, 2018.

Second Office Action issued in Chinese family member Patent Appl. No. 201580041498.9, dated Jul. 6, 2018.

Search Report issued in International Bureau of WIPO Patent Application No. PCT/EP2015/067155, dated Feb. 10, 2015.

Notification of Rejection Decision issued in Chinese family member Patent Appl. No. 201580041498.9, dated Aug. 1, 2019.

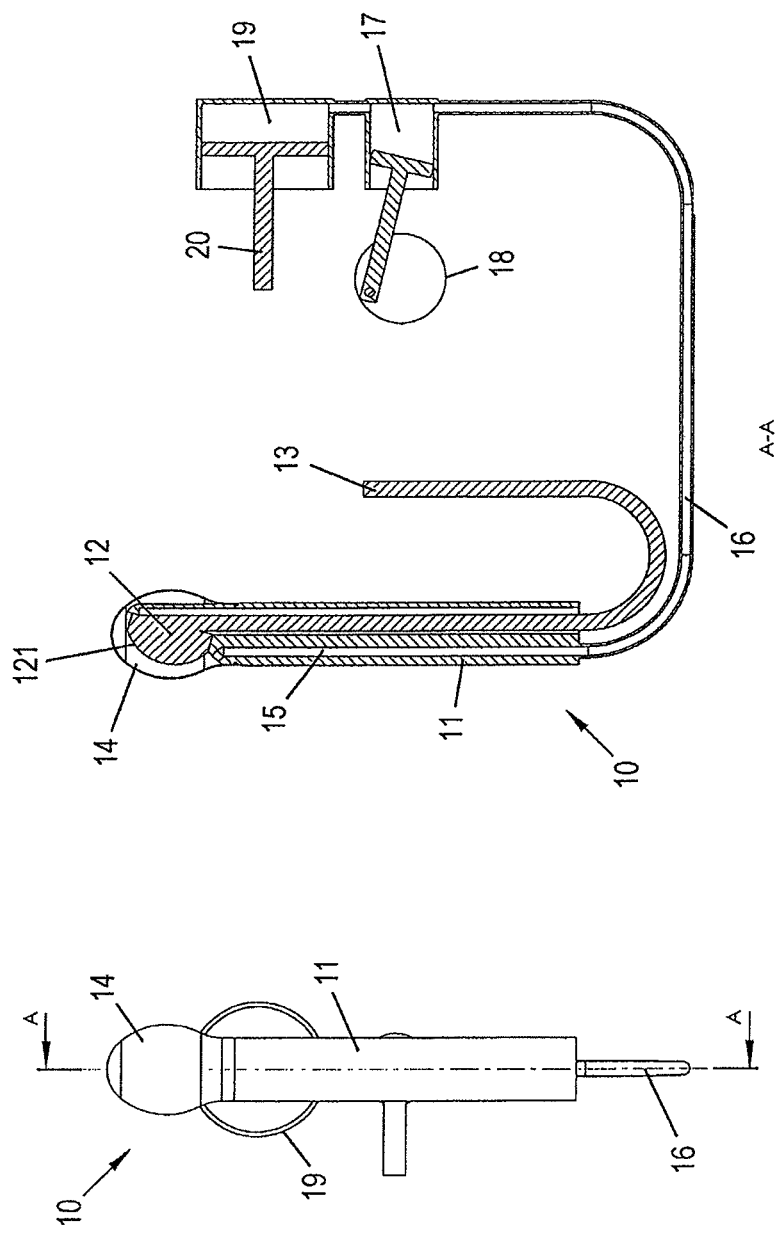

ENDOSCOPIC DEVICE

The present invention relates to an endoscopic device to be inserted into a body cavity.

What is known is an endoscope as an instrument that is inserted into a region to be examined, which is sometimes difficult to access and usually not illuminated, such as a tunnel-shaped lumen (colon, esophagus, etc.), so as to get an overview of this region to be examined. The region to be examined is imaged by means of cameras, for example, and the image information is made available to the examining person.

PROBLEM TO BE SOLVED BY THE INVENTION

The present invention is aimed at improving such an endoscope. In particular, it is the object of the present invention to provide an endoscopic device capable of Advantageously providing information on a region to be examined.

SOLUTION TO THE PROBLEM

According to the invention, this problem is solved by an endoscopic device comprising the features of claim 1.

Advantageous further developments are described in the dependent claims.

Thus, the invention relates to an endoscopic device to be inserted into a body cavity, comprising an elastographic recording means, an inflatable body and a device for rhythmically changing the volume of the inflatable body.

Such an endoscopic device enables an elastographic examination inside the body.

In elastography, a relatively new discipline of ultrasonic diagnostics, the doctor rhythmically presses the sonic head on the region to be examined. While doing so, hard tissue parts are not as much compressed as soft parts. The relative movements of the tissue portions can be calculated by means of image processing. Hence, hard and soft tissue portions can be differently colored on the screen. Cancerous tissue is usually harder than the surrounding tissue and can thus be diagnosed.

Inside of a body cavity, the examining doctor cannot apply a rhythmical pressure on the tissue in a conventional manner. In the case of the endoscopic device according to the invention, the inflatable body, which is needed anyway to couple the sound to the tissue, can be used specifically for this purpose. By means of the device for rhythmically changing the volume of the inflated inflatable body, the volume of the balloon catheter can be rhythmically changed. By alternating expansion and contraction of the inflatable body a pressure can be exerted on the surrounding tissue. Hard and soft tissue portions will then react differently to the pressure applied on the tissue. Soft tissue portions will yield more easily and/or stronger than hard tissue portions. This different yielding can be elastographically recorded and taken into consideration in the course of a possible treatment.

In the endoscopic device, the device for rhythmically changing the volume of the inflatable body operates using a volume change frequency suitable for an elastographic recording.

The volume change frequency can, for example, be 1-2 Hz, with a range between 0.1-1 Hz being also possible. Basically, an arbitrary volume change frequency suitable for an advantageous elastographic recording can be applied; this arbitrary volume change frequency is technically applicable under consideration of a flow resistance between the device for rhythmically changing the volume of the inflatable body and the inflatable body.

In the endoscopic device, the elastographic recording means can be an ultrasonic head (sonography). The principle of the invention can also be applied to other elastographic recording means in which other types of signals (audible sonic waves, infrasound, light, etc.) are used. It is merely necessary that in the tissue to be examined the hard and soft tissue portions detected by changing the volume of the inflatable body abutting the tissue are recorded by the signals with sufficient accuracy.

In the endoscopic device, the inflatable body may be a balloon catheter disposed at the outer circumference of the endoscopic device. A camera, an illumination means, an image sensor or another optical means could then be arranged at the distal end of the endoscopic device.

In the endoscopic device, the inflatable body can alternatively be a balloon catheter disposed at the distal end of the endoscopic device. In this case, a camera, an illumination means, an image sensor or another optical means could be arranged proximally of the inflatable body.

In the endoscopic device, the device for rhythmically changing the volume of the inflatable body can be an alternating pressure generator which applies an alternating pressure to a pressure medium provided in the inflatable body in an inflation state of the inflatable body. The pressure medium may be water, a saline solution, a water-containing gel or another liquid tolerable by the body to be examined. The pressure medium transmits the signal waves of the elastographic recording means.

In the endoscopic device, the alternating pressure generator can be disposed at the proximal end of the endoscopic device and can be connected to the inflatable body via a pressure transmission channel provided in the endoscopic device.

In the endoscopic device, the alternating pressure generator may be arranged adjacent to the inflatable body and operable mechanically or via a signal line leading to a portion of the endoscopic device, which is not inserted into the body cavity.

In the endoscopic device, the alternating pressure generator may be a pump, a piston or an accumulator switchable between two different pressures.

In the endoscopic device, the device for rhythmically changing the volume may be disposed between the inflatable body and a pressurizing device for inflating the inflatable body.

The endoscopic device may be provided with an illumination means and an image sensor, which are arranged and aligned in such a way that they can illuminate and image the region with which the inflatable body comes into abutment in the body cavity. Hence, the information detected by the elastographic recording means can be combined with image information so as to quickly and reliably gain an insight into the state of the tissue in question.

The endoscopic device may be a flexible or a rigid endoscope. Thus, the present invention can be flexibly applied to a plurality of endoscopic devices.

The features of the invention can be combined appropriately.

Subsequently, the invention is described in detail using examples.

BRIEF DESCRIPTION OF THE DRAWINGS

FIG. 1 shows an embodiment of an endoscopic device according to the invention.

The embodiments of the present invention are described in the following.

EMBODIMENT

Subsequently, an embodiment is explained by referring to FIG. 1.

FIG. 1 shows an embodiment of an endoscopic device according to the invention. In particular, the left side of FIG. 1 shows a side view of the endoscopic device of the embodiment. Moreover, the right side of FIG. 1 shows a sectional view along the line A-A of the endoscopic device illustrated on the left side, as top view.

The endoscopic device 10 of the embodiment has an elongated endoscope shaft 11 which is insertable into a cavity to be examined. The endoscope shaft 11 may be rigid or flexible.

An ultrasonic transducer (ultrasonic head) 12 comprising an appropriate number of ultrasonic cells 121 is disposed at the distal end of the endoscope shaft 11. Upon application of an excitation command, the ultrasonic cells 121 can transmit ultrasonic waves. The ultrasonic transducer 12 comprising the ultrasonic cells 121 functions as ultrasonic probe and transmits and receives the ultrasonic waves, converts them into electrical impulses and transmits the same for processing. For this purpose, the ultrasonic transducer 12 is connected to an ultrasonic transducer cable 13. In the ultrasonic transducer cable 13, the obtained electrical impulses generated from the received reflected ultrasonic waves can be transmitted to a processing unit or a display unit, which are not shown. In the ultrasonic transducer cable 13, the excitation command for exciting the ultrasonic cells 121 can also be transmitted via a separate line. Alternatively, the line for transmitting the excitation command for exciting the ultrasonic cells 121 may be a line separate from the ultrasonic transducer cable 13.

In FIG. 1, as illustrated on the right, the ultrasonic transducer 12 is shown in such a way that it has the ultrasonic cells 121 on the side facing towards the viewer, on the side facing to the left, on the side facing away from the viewer and on the side of the ultrasonic transducer 12 facing upwards (distal side). Alternatively, the ultrasonic transducer 12 can also be designed such that it additionally comprises ultrasonic cells 121 on the side of the drawing facing to the right. In a further alternative, the ultrasonic cells 121 of the ultrasonic transducer 12 can also be arranged at any arbitrarily selected region of the above-mentioned arrangement regions.

An inflatable balloon 14 is disposed around the distal outer circumference of the ultrasonic transducer 12. The inflatable balloon 14 is formed as a balloon catheter and can be made of a suitable plastic material and be transparent, for example. The inflatable balloon 14 can be made of a stretchable or non-stretchable plastic material which, under pressure load due to inflation, appropriately clings to the wall, which is to be examined, of the cavity to be examined. The inflatable balloon 14 is disposed around the outer circumference of the ultrasonic transducer 12 at least in a manner such that it can be spaced apart from the ultrasonic cells 121.

On its proximal side, the inflatable balloon 14 is connected to a balloon inflating channel 15 extending in parallel to the extension of the endoscope shaft 11 and inside thereof. The balloon inflating channel 15 may be a cavity in the endoscope shaft 11 or formed as a tube fixedly inserted into the endoscope shaft 11.

At the proximal end of the balloon inflating channel 15, the balloon inflating channel 15 is connected to a balloon inflating pipe 16 connecting the balloon inflating channel 15 with a subsequently described device for rhythmically changing the volume of the inflatable body.

When the inflatable balloon 14 is inflated, it is spaced apart from the ultrasonic cells 121.

The inflatable balloon 14 is fixed, for example by gluing, fusing or another appropriate method, to the outer circumference of the endoscope shaft 11, in a manner sufficiently spaced apart from the ultrasonic cells 121.

The material of the inflatable balloon 14 can alternatively extend from the portion, at which it is fixed to the outer circumference of the endoscope shaft 11, up to the proximal end of the endoscope shaft 11 at the outer circumference of the endoscope shaft 11 and, thus, form a sheath of the endoscope shaft 11.

The device for rhythmically changing the volume of the inflatable body, described in the embodiment as pump 17 for impulse application, is connected at the proximal end of the balloon inflating pipe 16. The pump 17 serves as alternating pressure generator and includes a cylinder in which a piston is driven via a pump driving device 18 to rhythmically move to and fro. The pump driving device 18 can be an electric motor or another appropriate drive source.

A pump 19 for inflating the balloon is disposed proximally (i.e. upstream) of the pump 17, so that it can apply pressure to the balloon inflating pipe 16. The pump 19 has a cylinder in which a cylinder-like piston 20 is seated so as to be movable to and fro. The piston 20 can be moved manually in the cylinder. Alternatively, the piston 20 can be moved in the cylinder by another suitable drive source. The piston 20 is moved in the cylinder of the pump 19, between a pressurizing position to the right in the drawing and a depressurizing position to the left in the drawing.

Hence, the pressure chamber of the pump 19 is connected to the pressure chamber of the pump 17 and the balloon inflating pipe 16.

A pressure medium is filled into the system comprising the pressure chamber of the pump 19, the pressure chamber of the pump 17, the balloon inflating pipe 16, the balloon inflating channel 15 and the inside of the balloon 14. The system is preferably sealed.

The pressure medium used is water, a saline solution, a water-containing gel or another liquid tolerable by the body to be examined.

When the balloon 14 is inflated (pressurizing position of the pump 19), the to-and-fro movement of the piston in the cylinder of the pump 17 causes a rhythmic change of the volume of the entire system comprising the pressure chamber of the pump 19, the pressure chamber of the pump 17, the balloon inflating pipe 16, the balloon inflating channel 15 and the inside of the balloon 14. Hence, the to-and-fro movement of the piston in the cylinder of the pump 17 causes a rhythmic change of the volume of the balloon 14. Thus, in the state pressurized (filled) by the pump 17, the volume of the balloon 14 is filled in an oscillating manner with the differential volume formed between the pressurizing position and the depressurizing position of the pump 19.

The invention is not restricted to the illustrated pump 17. Any other device capable of rhythmically changing the volume of the balloon 14 may be used instead of the pump 17.

Also the pump 19 can have an arbitrary structure as long as it is capable of applying a pressure to the system comprising the pressure chamber of the pump 19, the pressure chamber of the pump 17, the balloon inflating pipe 16, the balloon inflating channel 15 and the inside of the balloon 14.

Function

In the depressurized state (in the drawing, the piston 20 of the pump 19 is moved out to the left), the endoscope shaft 11 is inserted into the cavity to be examined to such an extent that the ultrasonic transducer 12 faces the cavity region to be examined.

The piston 20 of the pump 19 is moved in to the pressurizing position of the pump 19 (to the right in the drawing). Thereby, a pressure is applied to the system comprising the pressure chamber of the pump 19, the pressure chamber of the pump 17, the balloon inflating pipe 16, the balloon inflating channel 15 and the inside of the balloon 14, and the balloon 14 is inflated. In particular, the piston 20 is moved in to such an extent that the balloon 14 tightly clings to the cavity wall of the cavity to be examined. The pressure is applied at least in such a manner that the balloon skin of the balloon 14 remains pressed against the tissue of the cavity also in the depressurized state of the pump 17.

If, due to pressurizing of the balloon 14, the balloon skin of the balloon 14 is tightly pressed against the cavity region to be examined, the driving of the pump driving device 18 of the pump 17 and, thus, the rhythmical change of the volume in the system comprising the pressure chamber of the pump 19, the pressure chamber of the pump 17, the balloon inflating pipe 16, the balloon inflating channel 15 and the inside of the balloon 14 is started. Thereby, the balloon skin of the balloon 14 is, alternatingly stronger and weaker, rhythmically pressed against the tissue of the cavity (in the same rhythm as the rhythmical change of the volume in the system).

Simultaneously with the rhythmical alternating loading of the balloon skin of the balloon 14 at the cavity tissue, the ultrasonic cells 121 are actuated and ultrasonic images of the cavity region to be examined are carried out, with the results being elastographically recorded.

The ultrasound-supported elastography is an imaging method which determines the elasticity of tissue and is able to represent it differently (e.g. in different colors), depending on the stretching degree. The ultrasound-supported elastography is based on the fact that hard tissue parts—such as tumorous tissue or cancerous tissue—deform less under pressure than soft tissue; in other words, these affected tissue portions are harder than healthy tissue. Due to the different stretching properties of tumorous and healthy tissue, the echo signals are minimally delayed in time. By means of a specific software, these are displayed in real time, for example in color, on a monitor of the not shown processing unit or display unit and conspicuous regions are marked in the ultrasonic image.

In this way, harder and, thus, possibly problematic tissue portions in the cavity region to be examined can be localized quickly.

Then, the pump 19 can be depressurized, causing the balloon skin of the balloon 14 to separate from the tissue of the cavity. Now, in the depressurized state of the pump 19, the endoscope shaft 11 can be inserted further into the cavity to be examined so as to examine another region of the cavity.

Advantages

The examination is short and pain-free. The device is cost-effective.

Due to the invention, local hardenings and tissue changes can be detected safely, quickly and reliably. This enables the experienced doctor to specifically take tissue samples. Thus, a second examination or a second biopsy may become superfluous.

The endoscopic device according to the invention can be used in the field of gastroscopy or colonoscopy.

Further Alternatives

A camera, an image sensor or the like can be disposed at the outer circumference of the endoscope shaft 11 of the endoscopic device 10 of FIG. 1, proximal of the inflatable balloon 14. If the balloon skin of the balloon 14 is transparent, a camera, an image sensor or the like may also be disposed in the region covered by the balloon skin of the balloon 14 at the distal end of the endoscope shaft 11, adjacent to the ultrasonic cells 121 at the ultrasonic transducer 12.

In a further alternative, a camera, an image sensor or the like can be disposed at the distal end of the endoscope shaft 11, and the inflatable balloon 14 can be disposed proximally of the camera, the image sensor, etc. at the outer circumference of the endoscope shaft 11.

The balloon skin of the balloon 14 does not have to be transparent.

In the embodiment, the pump 17 for impulse application, the pump driving device 18, the pump 19 for inflating the balloon and the piston 20 are provided proximally of the endoscope shaft 11 and are connected to the endoscope shaft 11 via the pipe 16. The invention is not restricted thereto. The pump 17 comprising the pump driving device 18 or the pump 17 comprising the pump driving device 18 and the pump 19 and the piston 20 can also be provided at the proximal end of the endoscope shaft 11 or, if appropriately miniaturized, at the outer circumference of the endoscope shaft 11.

In the embodiment, the pump 17 comprising the pump driving device 18 is used as alternating pressure generator. The alternating pressure generator can also be a completely differently structured pump, a piston or an accumulator switchable between two different pressures. The alternating pressure generator must merely be capable of rhythmically changing the volume of the inflated balloon 14 advanced to the tissue.

In the endoscopic device, this alternating pressure generator can even be disposed adjacent to the balloon 14 or inside the balloon 14 and operable mechanically or via a signal line leading to a portion of the endoscopic device which is not inserted into the body cavity.

In the embodiment, the balloon 14 is fixedly disposed at the outer circumference of the endoscope shaft 11. However, the balloon 14 does not necessarily have to be fixedly connected to the endoscope. Instead, it may also be a disposable balloon which is thrown away after every examination. The endoscope is then provided with one appropriate groove or several grooves into which the balloon 14 can engage. The balloon 14 itself can then be provided with a reinforcement or an engagement ring at the proximal end, the reinforcement/the engagement ring engaging with the groove or the grooves when arranging a new balloon 14 on the endoscope shaft 11.

LIST OF REFERENCE SIGNS

10 endoscopic device
11 endoscope shaft 12 ultrasonic transducer
121 ultrasonic cell
13 ultrasonic transducer cable
14 inflatable balloon
15 balloon inflating channel
16 balloon inflating pipe
17 pump for impulse application
18 pump driving device
19 pump for inflating the balloon
20 piston

The invention claimed is:

1. An endoscopic device to be inserted into a body cavity, comprising
 an elastographic recorder,
 an inflatable body, and
 a first pump that rhythmically changes the volume of the inflatable body;
 a second pump that inflates the inflatable body, wherein the second pump is positioned downstream of the first pump and is disposed proximally of the first pump.

2. The endoscopic device according to claim 1, wherein the first pump operates at a volume change frequency suitable for an elastographic recording.

3. The endoscopic device according to claim 1, wherein the elastographic recorder is an ultrasonic head.

4. The endoscopic device according to claim 1, wherein the inflatable body is a balloon catheter disposed at the outer circumference of the endoscopic device.

5. The endoscopic device according to claim 1, wherein the inflatable body is a balloon catheter disposed at the distal end of the endoscopic device.

6. The endoscopic device according to claim 1, wherein the first pump applies an alternating pressure to a pressure medium provided in the inflatable body in an inflation state of the inflatable body.

7. The endoscopic device according to claim 6, wherein the pressure medium for inflating the inflatable body is water, saline solution or another liquid tolerable by the body to be examined.

8. The endoscopic device according to claim 1, wherein the first pump is disposed at the proximal end of the endoscopic device and connected to the inflatable body via a pressure transmission channel provided in the endoscopic device.

9. The endoscopic device according to claim 1, wherein the first pump is disposed adjacent to the inflatable body and operable mechanically or via a signal line on a portion of the endoscopic device, which portion is not inserted into the body cavity.

10. The endoscopic device according to claim 1, wherein the first pump is switchable between two different pressures.

11. The endoscopic device according to claim 1, further comprising:
 an illuminator and an image sensor disposed and aligned such that the illuminator can illuminate and the image sensor can display the region with which the inflatable body comes into abutment in the body cavity.

12. The endoscopic device according to claim 1, wherein the endoscopic device is a flexible or a rigid endoscope.

* * * * *